United States Patent
Holms

(12) 
(10) Patent No.: US 6,322,362 B1
(45) Date of Patent: Nov. 27, 2001

(54) DENTAL INSTRUMENT

(76) Inventor: Allan G. Holms, 1314 S. Grand #2-112, Spokane, WA (US) 98202

( * ) Notice: Subject to any disclaimer, the term of this patent is extended or adjusted under 35 U.S.C. 154(b) by 0 days.

(21) Appl. No.: 09/048,965

(22) Filed: Mar. 26, 1998

(51) Int. Cl.$^7$ .................................................. A61C 17/00
(52) U.S. Cl. ................................. 433/143; 433/141
(58) Field of Search ....................... 433/141, 143, 433/147

(56) References Cited

U.S. PATENT DOCUMENTS

| | | | |
|---|---|---|---|
| Re. 34,196 | 3/1993 | Munro | 433/215 |
| D. 336,517 | 6/1993 | McKeown | D24/133 |
| D. 380,265 | 6/1997 | Mark | D24/152 |
| 4,030,199 * | 6/1977 | Russell | 433/147 |
| 4,283,808 | 8/1981 | Beebe | 15/145 |
| 4,416,166 * | 11/1983 | Jannard et al. | 74/551.9 |
| 4,552,531 | 11/1985 | Martin | 433/147 |
| 4,721,021 * | 1/1988 | Kusznir | 81/22 |
| 4,739,536 * | 4/1988 | Bandera et al. | 16/111 R |
| 4,743,198 * | 5/1988 | Kennedy | 433/143 |
| 4,759,713 | 7/1988 | Heiss et al. | 433/141 |
| 4,820,154 | 4/1989 | Romhild et al. | 433/128 |
| 4,949,457 * | 8/1990 | Burout, III | 30/85 |
| 4,990,089 | 2/1991 | Munro | 433/215 |
| 5,030,091 | 7/1991 | Svanberg | 433/143 |
| 5,090,907 * | 2/1992 | Hewitt et al. | 433/143 |
| 5,169,313 * | 12/1992 | Kline | 433/143 |
| 5,169,314 | 12/1992 | Long | 433/143 |
| 5,328,370 | 7/1994 | Chen | 433/147 |
| 5,339,482 * | 8/1994 | Desimone et al. | 15/167.1 |
| 5,350,927 | 9/1994 | Rakhimov et al. | 250/504 |
| 5,390,572 * | 2/1995 | Gakhar et al. | 81/436 |
| 5,398,369 * | 3/1995 | Heinzelman et al. | 15/167.1 |
| 5,472,720 | 12/1995 | Rakhimov et al. | 426/241 |
| 5,486,109 | 1/1996 | Hunter et al. | 433/72 |
| 5,501,597 | 3/1996 | Wilson | 433/141 |
| 5,624,259 | 4/1997 | Heath et al. | 433/72 |
| 5,707,911 | 1/1998 | Rakhimov et al. | 501/128 |
| 5,781,958 * | 7/1998 | Meessmann et al. | 433/141 |
| 5,816,806 | 10/1998 | Herbst et al. | 433/141 |

FOREIGN PATENT DOCUMENTS

| | | | |
|---|---|---|---|
| 2659846 * | 9/1991 | (FR) | 433/143 |

OTHER PUBLICATIONS

Pfinest & Company, Inc., "Complete Pfinest 1983 Catalog No. 33 Dental Instruments and Laboratory Supplies" p. 91, 1983.*

Pearson dental equipment catalog, pp. 212, 213, 216, 217, 218, 225 (no date).

* cited by examiner

*Primary Examiner*—Ralph A. Lewis
(74) *Attorney, Agent, or Firm*—Stratton Ballew PLLC

(57) ABSTRACT

An apparatus for a dental instrument and specifically for a dental curette. The dental instrument comprises a handle having a first end and a second end. The handle has a substantially elongate form, and is molded from a composite of nonmetallic components. The handle also includes a first tip and a second tip that are received into the first end and the second end of the handle, respectively. The first tip and the second tip include metal tools, preferably formed from a stainless steel. The handle includes a core component comprising of a substantially rigid material, and a grip component comprising of a substantially elastic material. Selected thermosetting or thermoplastic polymeric casting resins, which are autoclaveable and chemclaveable, provide the desired tactile and structural qualities for the core component and the grip component.

4 Claims, 6 Drawing Sheets

DENTAL INSTRUMENT

TECHNICAL FIELD

The invention comprises a dental instrument having novel features and a method for manufacturing the dental instrument that includes unique combinations of material compositions and ergonomic features that provide comfort and versatility. More particularly, the present invention comprises a dental curette formed from a composite of elastomeric materials that can withstand conventional heat sterilization methods.

BACKGROUND OF INVENTION

Modern dentistry has spawned a wide variety of hand-held instruments specifically tailored for manual procedures commonly performed by a dentist or hygienist. One broad classification of such manually employed dental instruments includes double ended instruments. Typically, these double ended instruments have a pencil-like handle with a specialized tool mounted to each end of the handle. This broad category of dental instruments is commonly referred to as curettes. For the purposes of the present invention, the category of curettes includes carvers and filling instruments, as well as specialized scrapers or scoops, commonly referred to as cleoids and discoids.

The conventional double ended dental instrument includes a handle having two tapered ends. Inserted into each of these ends are tips. The tips are designed for specific and specialized tasks. The user, typically the dentist or hygienist, may require differing sizes, diameters, and shapes of tips to perform any particular dental procedure. The need for efficient, precise and well-designed dental instruments has resulted in many patents issued for improvements on the basic and conventional design.

U.S. Pat. No. 4,552,531 to Martin shows an example of a conventional dental instrument with a simple improvement in its tip system. The conventional, rod-like handle of Martin '531 includes a cross hatched knurling. The handle also includes sockets at each end for receiving tips. The tips of Martin '531 are replaceable with a novel "snap-fit" mechanism. As disclosed by Martin '531, the tips are preferably made from conventional materials such as stainless steel or chrome plated brass, and still fit into a handle that presents problems for the user. When a user must hold a metal instrument of a small diameter for an extended period of time, the user will likely begin to show some sign of chronic fatigue in the finger muscles.

Improvements relating to the handle of the dental instrument often are directed toward improving the grip. The conventional metal handle, even when engraved with cross hatching or knurling, is difficult to hold onto when wet or when the user is wearing protective gloves, as is normally the case. U.S. Pat. No. 5,501,597 to Wilson discloses a dental instrument with gripping handles formed from an elastomeric material. The Wilson '597 gripping handle material is applied onto the ends of a "typical" dental instrument having an elongate shaft and knurled surfaces. Wilson '597 only teaches the utilization of an elastomeric gripping handle on a typical dental instrument, and more specifically only teaches the addition of the gripping handles to the end portions of the handle.

Typical dental instruments are manufactured by milling or grinding a block or rod of material into a desired shape, typically a pencil-like shape. Injection molding is an alternative to conventional milling and grinding for the manufacturing of the dental instrument's handle. Injection molding is discussed in U.S. Pat. No. 5,682,665 to Svanberg. Svanberg '665 discloses an injection mold process for manufacturing a dental curette. The Svanberg '665 method employs a metal injection molding process that results in an instrument of a unitary construction. Additionally, Svanberg '665 briefly suggests that ceramic or thermoplastic powders could be used in injection molding. Svanberg '665 also teaches color coding the instrument for identification of the curette blade's particular configuration. A problem with the Svanberg '665 method is that it can only produce a dental instrument composed from a single, homogenous material. No single material can provide the required properties for the tips, handles and grips that are needed in a precision dental instrument. A need exists for an injection molded dental instrument formed from more than a single material.

A two material, metal and plastic dental instrument is found in U.S. Pat. No. 4,759,713 to Heiss et al. Heiss et al. '713 discloses a disposable dental tool manufactured by over-molding or insert-molding a handle about a wire. While suggesting plastic materials, the Heiss et al. '713 instrument is designed for one-time, single patient, disposable use. Heiss et al. '713 teaches that these plastic handle materials will degrade when sterilized by conventional heat sterilization techniques.

As the U.S. Pat. No. 5,090,907 to Hewitt et al. teaches, dental instruments are typically held by the hand with the tip of the middle finger pressed upon the tapered portion of the handle. Hewitt et al. '907 discloses a dental curette having a finger pad mounted to the tapered tip of the curette's shaft. To be effective, Hewitt et al. '907 teaches that a finger gripping aid must extend to the tapered portion of the handle. Hewitt et al. '907 adds a bulbous finger pad to a conventional dental instrument to achieve this added finger gripping ability. A dental instrument is needed that reduces fatigue and the occurrence of chronic tendon, joint and muscle injury commonly associated with the long term occupational use of conventional dental instruments.

In an alternative, Hewitt et al. '907 suggests that a sleeve of resilient material could be utilized. The resilient material is taught by Hewitt et al. '907 to be silicone rubber or plastic. Hewitt et al. '907 is somewhat similar to Wilson '597 in design and importantly only teaches the retrofit of conventional metal dental instruments with their finger grips.

Additionally, although Heiss et al. '713 does suggest radiation and ethylene oxide sterilization as an alternative sterilization to make the instrument reusable, these sterilization techniques are neither widely available nor accepted, primarily due to environmental health concerns. Therefore, a molded dental instrument is needed that can be reused after sterilization with conventional heat sterilizing techniques.

U.S. Design Pat. No. 33,517 to McKeown, shows a dental instrument handle with apparent ergonomic features, but also includes rows of bumps on what appears to be the grip portion of the handle. The ornamental bumps of McKeown '517 also appear to have a functional purpose, potentially improving a user's frictional grip upon the instrument. However, the bumps on the handle of the McKeown '517 instrument are only present at the middle portion of the handle. Additionally, for sterilization purposes, Hewitt et al. '907 teaches that the finger pad is removable. An ergonomic dental instrument handle is needed that includes true finger gripping features, rather than the ornamental features of McKeown '517, but with non-removable finger grips permanently incorporated into a sterilizable dental instrument.

Seemingly ornamental features would be advantageous in the tracking and personalization of a particular instrument if such features would be resistant to autoclaving and chemclaving environments. A personalized and trackable dental curette is needed that is easily distinguishable and trackable for use by or as belonging to specific doctors or technicians, and for specific purposes or procedures.

SUMMARY OF INVENTION

The present invention provides an improved dental instrument and specifically an improved dental curette. The dental instrument comprises a handle having a first end and a second end. The handle has a substantially elongated form, and is molded from a composite of nonmetallic components. The handle also includes a minimum of a first tip that is received into the first end of the handle. In a dental curette, the first tip includes a metal tool, preferably formed from a stainless steel. The first tip is permanently received into the first end of the handle or as an alternative, interchangeably replaced.

Similarly, the handle can also include a second tip that is received into the second end of the handle. The second tip also includes a metal tool, preferably formed from a stainless steel. The second tip is permanently received into the second end of the handle or as an alternative, interchangeably replaced.

The handle includes a core component and a grip component. The core component of the handle formed from a substantially rigid material, and the grip component is comprised of a substantially elastic material. Selected thermosetting or thermoplastic polymeric casting resins can be utilized to provide the desired qualities for the core component and the grip component.

Also alternatively, autoclave and chemclave resistant colored rings can be insertably received into the handle to provide distinctive and unique markings.

According to one aspect of the invention, a dental curette is provided with a composite handle that includes a substantially rigid core and a substantially elastic grip, selected for desired tactile and structural qualities, thereby providing a light weight and rigid dental curette with a comfortable grip. The dental curette reduces fatigue and the occurrence of chronic tendon, joint and muscle injury commonly associated with the long term occupational use of conventional dental instruments.

According to another aspect of the invention, the handle of the dental curette has the advantages of a "plastic" dental instrument, but with the added and novel advantage of the ability to withstand the high heat and harsh environments encountered in autoclave and chemclave environments.

According to yet another aspect of the invention, the composite handle of the dental curette is provided with autoclave and chemclave resistant markings, allowing the user to track and distinguish particular curettes as belonging to or as used by specific doctors or technicians, for specific purposes or procedures.

The invention will be better understood by reference to the following detailed description taken in conjunction with the accompanying drawings.

DETAILED DESCRIPTION OF SPECIFIC EMBODIMENTS

The present invention provides a dental instrument having novel features and a method for manufacturing the dental instrument that includes a unique combination of material compositions and ergonomic features that provide comfort and versatility. More particularly, the present invention comprises a dental curette having a handle formed from a composite of thermosetting polymeric materials that can withstand conventional heat sterilization methods.

Figures 1, 2:
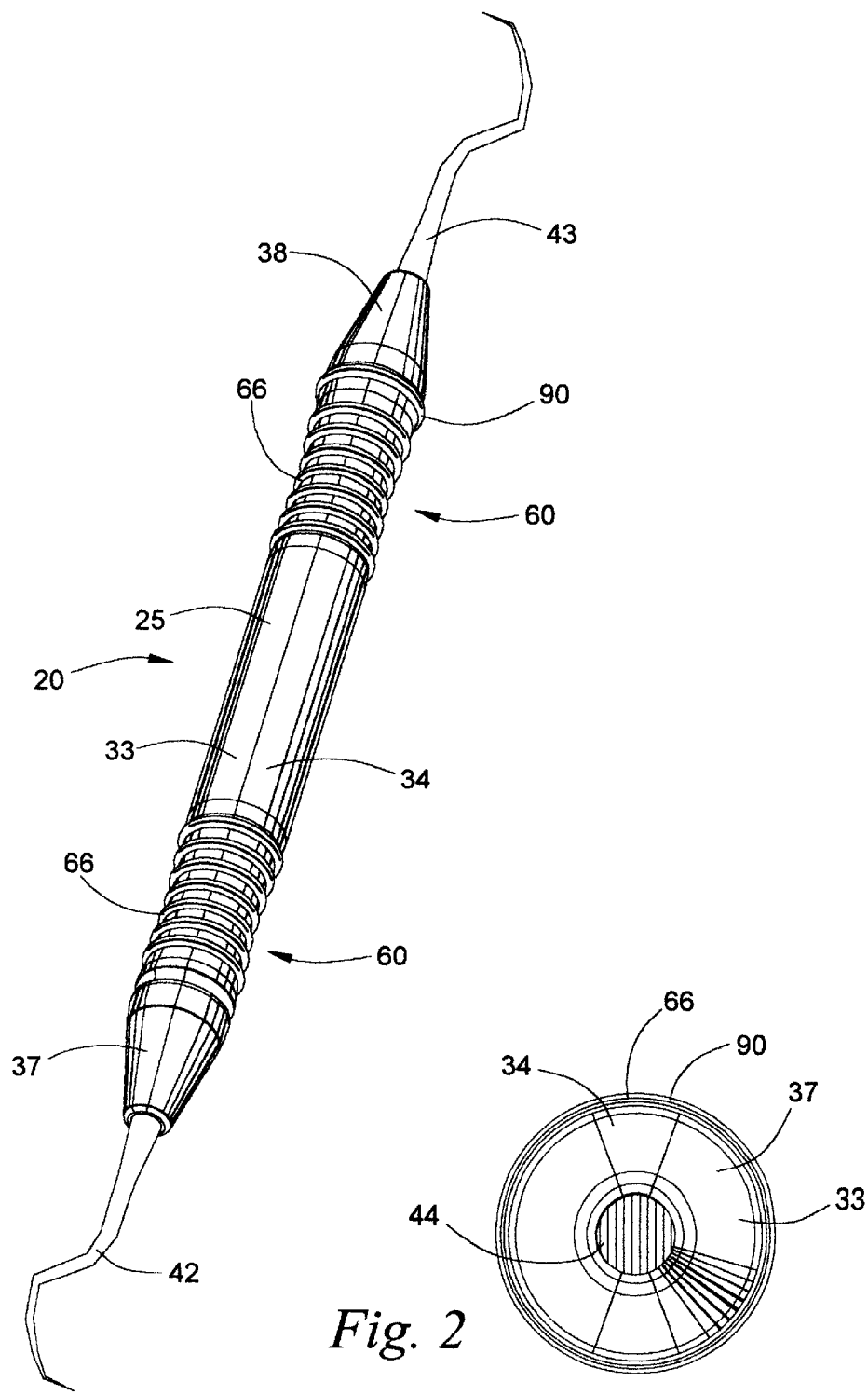
FIG. 1 is a perspective view of a dental instrument, according to an embodiment of this invention.
FIG. 2 is an end view of a dental instrument handle, according to the embodiment of this invention as shown in FIG. 1.

The present invention is shown in FIGS. 1 through 18. A preferred embodiment of the dental curette 20 is shown in FIG. 1. The dental curette includes a handle 25. The handle has a substantially elongated form and is molded from a composite of nonmetallic components.

Figure 6:
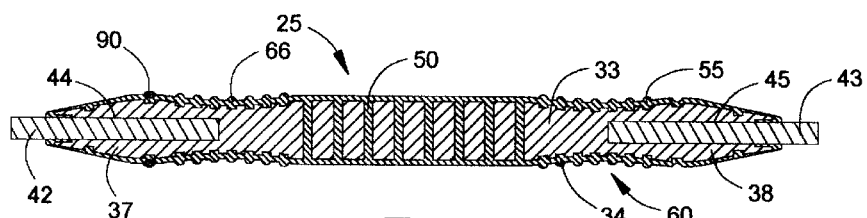
FIG. 6 is a sectioned view of a dental instrument, taken in the direction of the arrows 6—6 in FIG. 5.
Figure 5:
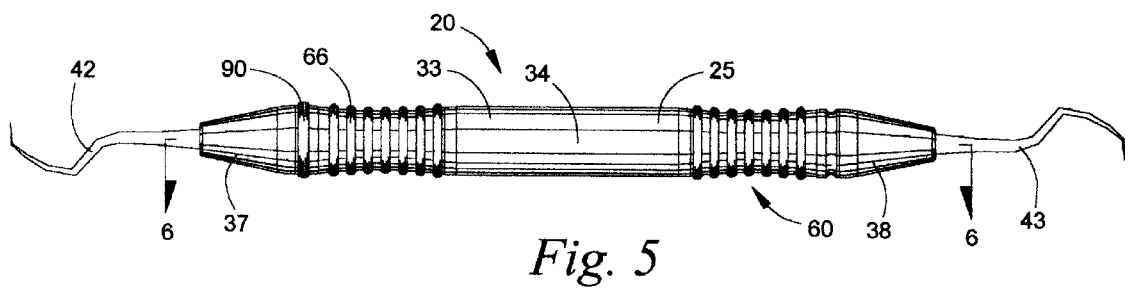
FIG. 5 is a top view of a dental instrument, according to the embodiment of this invention as shown in FIG. 1
Figure 4:
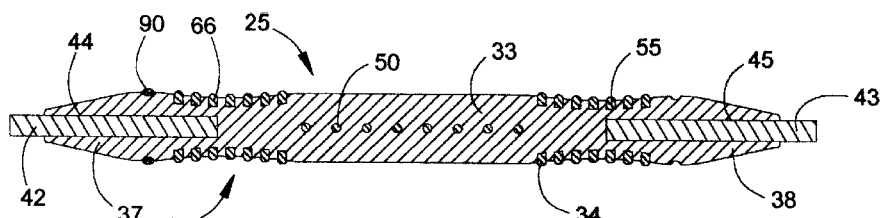
FIG. 4 is a sectioned view of a dental instrument handle, taken in the direction of the arrows 4—4 in FIG. 3.
Figure 3:
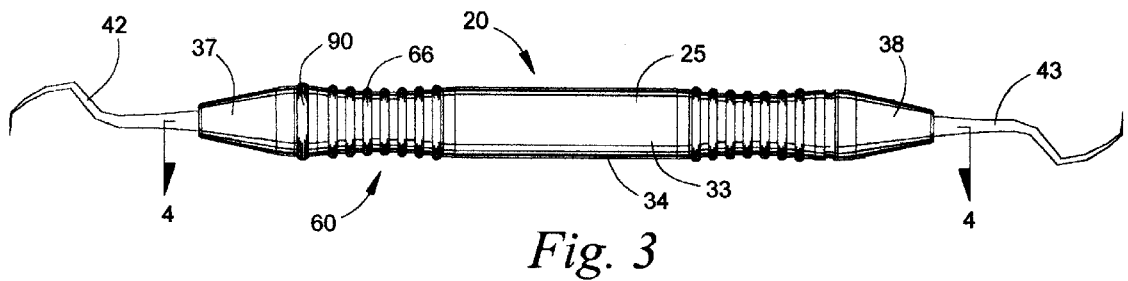
FIG. 3 is a side view of a dental instrument, according to the embodiment of this invention as shown in FIG. 1.
Figures 7, 8:
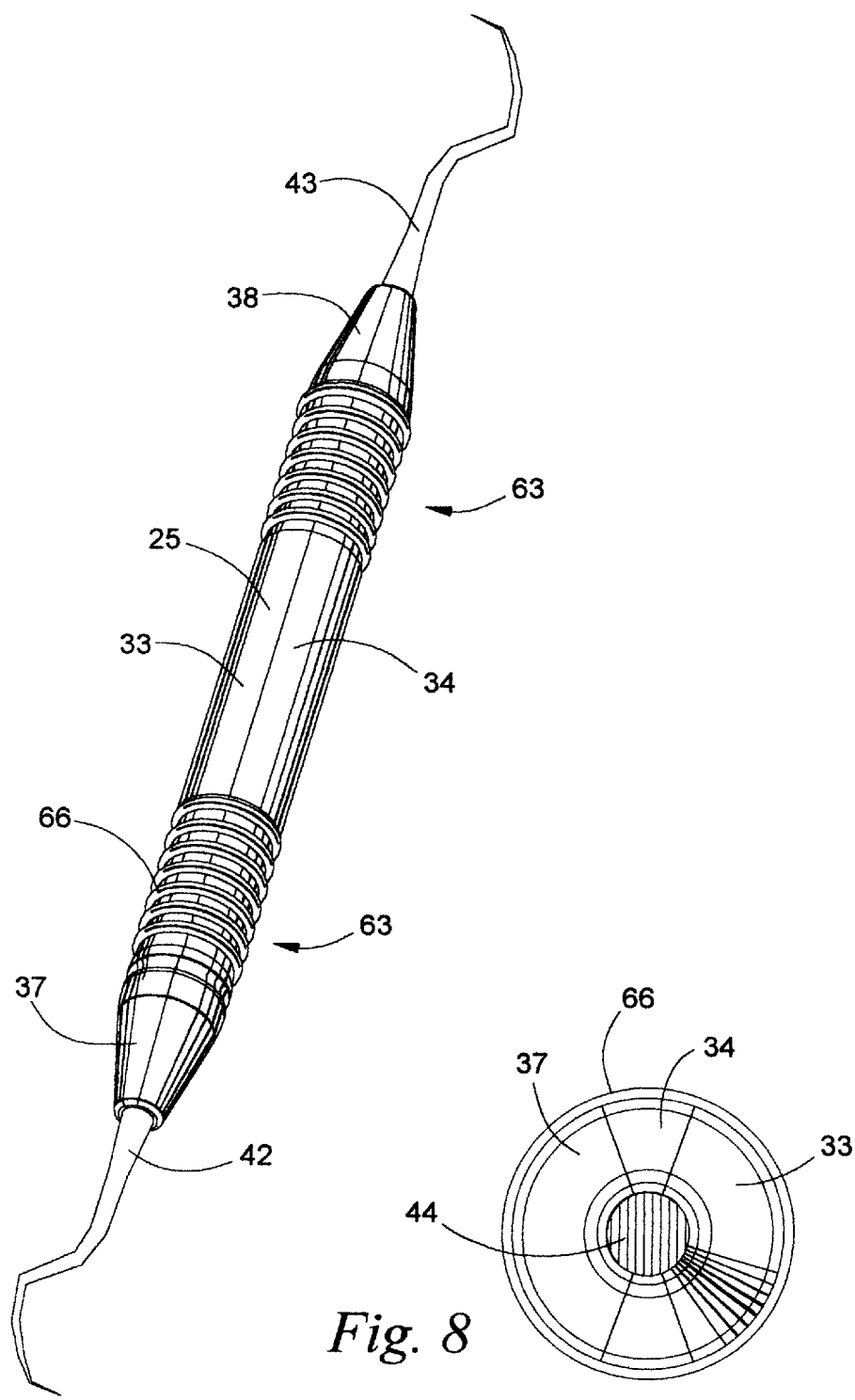
FIG. 7 is a perspective view of a dental instrument, according to an alternative embodiment of this invention.
FIG. 8 is an end view of a dental instrument, according to the alternative embodiment of this invention as shown in FIG. 7.
Figure 12:
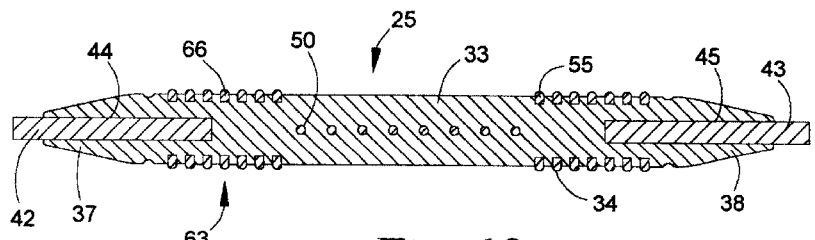
FIG. 12 is a sectioned view of a dental instrument, taken in the direction of the arrows 12—12 in FIG. 11.
Figure 11:
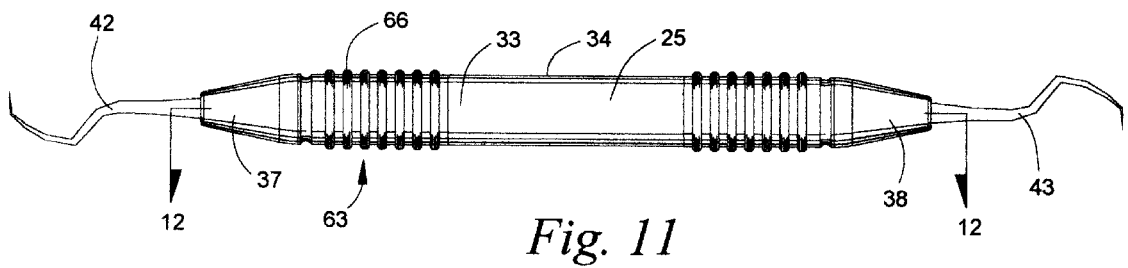
FIG. 11 is a side view of a dental instrument, according to the alternative embodiment of this invention as shown in FIG. 7.

As detailed in FIGS. 4 and 6, the handle 25 includes a core component 33 and a grip component 34. The core component is formed of a substantially rigid material, while the grip component is formed of a substantially elastic material. The core component and the grip component of the handle can also be observed from the exterior of the dental curette, as shown in FIGS. 1, 2, 3 and 5. The handle also has a first end 37 and a second end 38. The core component, being substantially rigid, minimizes flex and performs as a firm anchor for the retaining of a first tip 42. The first tip is receivable into a first socket 44 within the first end of the handle. Preferably, the handle can also receive a second tip 43. The second tip is receivable into a second socket 45 within the second tip of the handle. The core component of the handle also serves as a firm anchor for the second tip.

The core component 33 is preferably formed from a thermally processed polymeric casting resin. The preferred polymeric material for the core component is selected to develop cross linkages when initially heated and molded into a desired form and to subsequently retain the desired form, even when subjected to harsh sterilization environments.

By its rigid nature, the core component 33 cannot provide a comfortable and yielding grip surface. The addition of the grip component 34 onto the core component augments the core component with a yielding surface that provides a comfortable grip for the user. The grip component is preferably formed from a thermosetting polymeric material. The preferred thermosetting polymeric material for the grip component is also selected to develop cross linkages when initially molded into a desired shape and subsequently retain the desired shape, even when subjected to harsh sterilization environments. A silicon rubber thermosetting material which can conform to the user's fingers and still withstand harsh sterilization environments is most preferred for the formation of the grip component.

Figure 10:
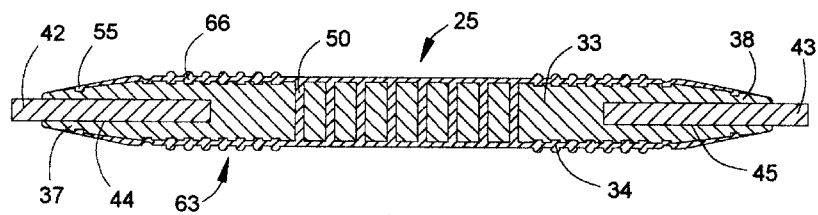
FIG. 10 is a sectioned view of a dental instrument, taken in the direction of the arrows 10—10 in FIG. 9.
Figure 9:
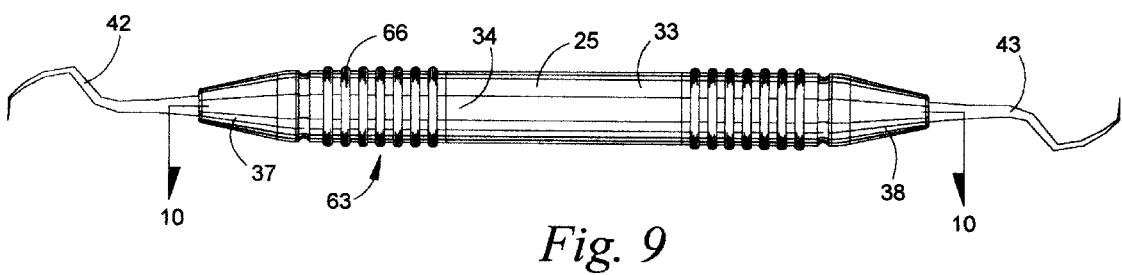
FIG. 9 is a top view of a dental instrument, according to the alternative embodiment of this invention as shown in FIG. 7.
Figures 13, 14:
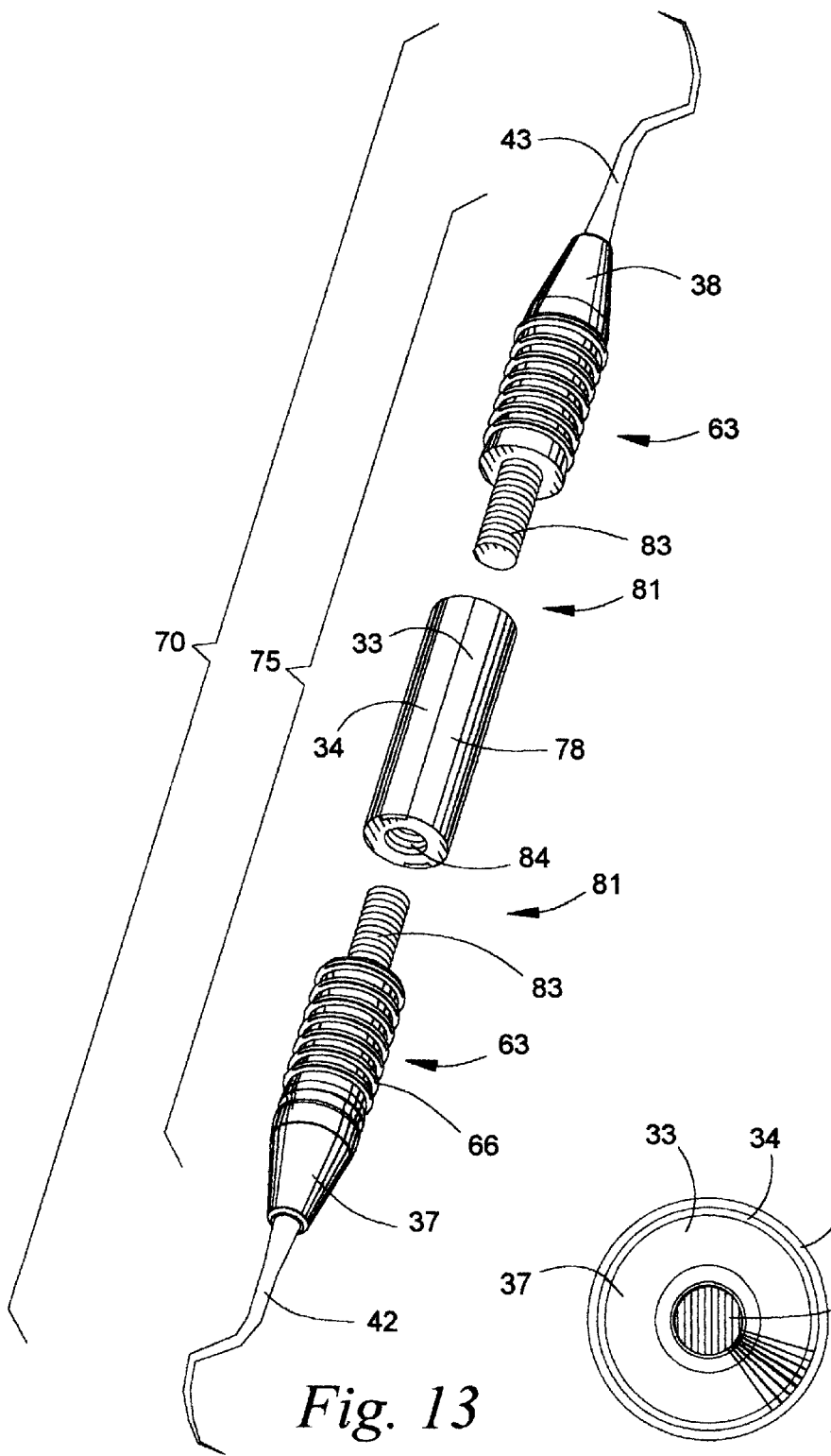
FIG. 13 is a perspective view of a dental instrument, according to an alternative embodiment of this invention.
FIG. 14 is an end view of a dental instrument, according to the alternative embodiment of this invention as shown in FIG. 13.
Figure 18:
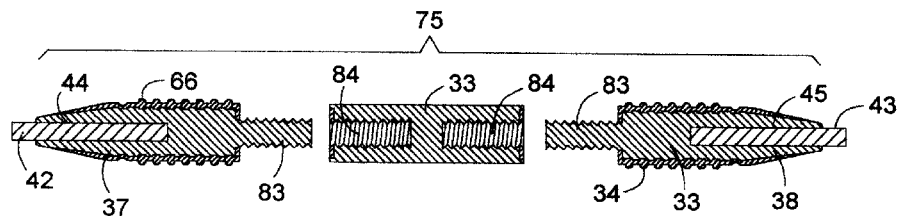
FIG. 18 is a sectioned view of a dental instrument, taken in the direction of the arrows 18—18 in FIG. 17.
Figure 17:
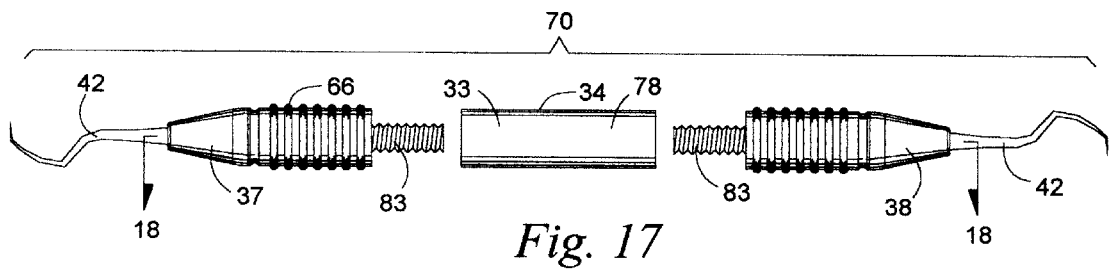
FIG. 17 is a side view of a dental instrument, according to the alternative embodiment of this invention as shown in FIG. 13.
Figure 16:
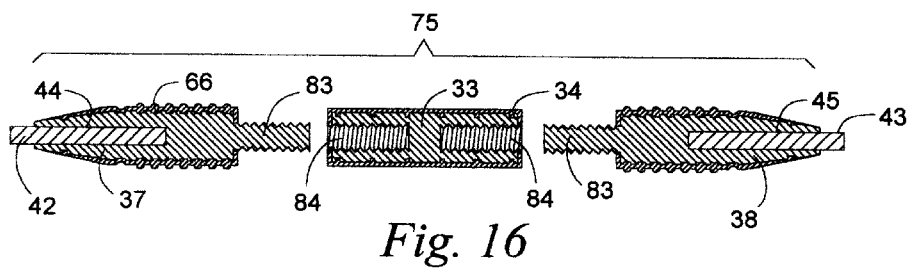
FIG. 16 is a sectioned view of a dental instrument, taken in the direction of the arrows 16—16 in FIG. 15.
Figure 15:
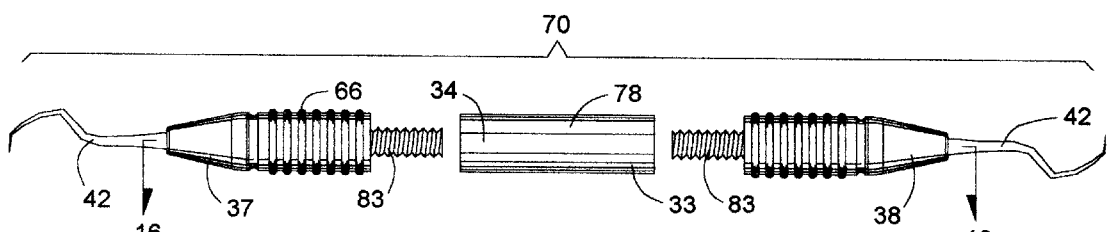
FIG. 15 is a top view of a dental instrument, according to the alternative embodiment of this invention as shown in FIG. 11.

A mechanical locking feature of the handle 25 is shown in FIGS. 10 and 13. The grip component 34 is "mechanically locked" onto the core component 33 by a series of channels 50, which penetrate the core component. Additionally, groves 55 within the core component facilitate the mechanical locking of the grip component to the core component of the handle.

This mechanical locking provides an additional resistive measure against the rigors of harsh sterilization environments. Harsh sterilization environments include all conventionally employed sterilization methods. The most common sterilization method is autoclaving. The autoclave utilizes high heat to effectively sterilize the instruments contained within. Most additional conventional sterilization methods include some form of chemclaving, such as ozone, ethylene oxide and glutaraldehyde sterilization. Ultraviolet and infrared sterilization are also considered by the inventor as potential sterilization methods that also require a selection of novel material combinations for the core component and the grip component of the present invention.

The first tip and the second tip are preferably formed from a stainless metal. The tip should be of surgical quality and hardness. More preferably, a martensitic stainless steel alloy is utilized. The martensitic stainless steel alloys are characterized by their ability to be quench tempered to achieve a high degree of hardness coupled with superior structural stability and toughness. Most preferably, the handle includes a minimum of a first tip 42. Conventionally, the first tip and the second tip 43 are metal tools, as shown in FIGS. 1–18. The metal tool is most preferably formed from a stainless alloy, such as ANSI type 440A martensitic stainless steel (UNS type S44002).

In another preferred alternative of the present invention, the core component 33 and the grip component 34 can be formed with materials having contrasting colors. The contrasting colors impart a unique and appealing appearance to the dental curette 20. Additionally, the colored dental curette is easily identified by the user as having a particular tip configuration, diameter or specialized use. Often in a dental office, several different doctors or hygienists share a common work area. The contrasting colored handles 25 of the dental curette help maintain separate identities of different user's instruments for efficient organization. The use of specific colored casting resins can also be employed to indicate instrument types, particular users, and increase appeal by being perceived as less intimidating to a patient in a dental office setting.

FIGS. 1 through 6 show a preferred alternative embodiment of the present invention that includes a tapered finger grip area 60. In an alternative embodiment of the present invention, this tapered finger grip area can be a straight grip area 63, as shown in the handle 25 of the dental curette 20 shown in FIGS. 7 through 12. Preferably the finger grip areas of the grip component 34 include ribs 66, as shown in FIGS. 1–18. The ribs are preferably ring-like features that aid the user in gripping the handle 25. The grip component, with the integral ribs, provide a soft gripping surface that adhesively contacts a user's fingers, especially when the user is wearing latex gloves. This ergonomic design reduces finger muscle fatigue in the user. Chronic problems, such as "Carpal-Tunnel Syndrome" that results from long term tendon, joint and muscle strain are also reduced.

FIGS. 13 through 18 show an alternative embodiment of a three-part dental curette 70. In this alternative embodiment of the dental curette 20 of the present invention, the three-part dental curette includes a three-part handle 75. Similar to the preferred handle 25, the three-part handle includes a first end 37 and a second end 38; however, the three-part handle also includes a main body 78.

The first tip 42 is received within the first end 37 of the main body 78 in the three-part dental curette 70, as shown in FIGS. 13 through 18. This removable attachment is preferably achieved with a disengageable coupling. Most preferably, as shown in FIG. 13, a threaded attachment 81 is utilized as the disengageable coupling. The threaded attachment is specifically shown in FIGS. 13, and 15 through 18. The removable first end 37 and second end 38 of the three-part dental curette include a threaded extension 83 that is received into a threaded socket 84 within the main body.

In this three-part alternative embodiment of the present invention, the first end 37 and the second end 38 can be interchangeably replaced with each other or with other ends. The tips of dental curettes, such as the first tip 42 and the second tip 43, are often in need of replacement or substitution. The specific procedure may require a different tip than first expected, or the tip may be dull or broken. Rather than disposing the instrument, sending it away for retooling, or maintaining an extensive array of instruments for every conceivable possibility, including backup instruments, the removable ends provide safety and convenience, while also reducing instrument inventory and replacement turnarounds, thereby providing an additional cost savings benefit.

Additionally, the three-part handle 75 of the three-piece dental curette 70, as shown in FIGS. 13 through 18, can be manufactured in a similar manner to the single piece handle 25, shown in FIGS. 1 through 12. To mold the handle of the dental curette 20, a conventional plastic injection mold machine is heated to a core component processing temperature. The core component processing temperature is an optimal mold temperature for the specific material selected to form the core component of the handle. A raw, core component material is selected and placed into the hopper of the mold machine. The raw core component material is fed by gravity into a screw bore, which is a barrel with a long variable flute screw. This screw mixes the raw core component material as it melts and prepares it for injection into the first mold.

Preferably, the core component 33 of the handle 25 is formed from a thermally processed polymeric casting resin.

Most preferably, the core component of said handle is formed from a thermosetting casting resin, or alternatively a thermoplastic casting resin. Casting resins considered by the inventor include nylon, polycarbonate, polyurethane or blended elastomeric materials.

In the raw state, casting resins are conventionally in the form of small pellets. These small pellets are melted into a homogeneous fluid for injection into a mold of the injection mold machine. The present invention requires a two-step injection mold process. A first step involves a first mold for forming the core component 33 and a second step that involves a second mold for the grip component 34 of the handle 20. The first mold is received into the mold machine and heated to the core component processing temperature. The mold machine closes upon the first mold and holds it closed at a clamping pressure. The clamping pressure must prevent the first mold from opening while the raw material is injected into the first mold. Once the first mold is closed, the homogeneously melted core component material is injected into the first mold under a high pressure. As the core component material flows into the first mold it fills all voids within the first mold to create the desired core component shape. When the first mold is full, it is held shut for a short time to allow curing of the core component material. After curing, the first mold is opened and the core component is ejected from the first mold.

The ejected core component 33 is then employed in the second mold where it is overmolded with a softer material. The process for this second step of the operation is the same as the first step, except that prior to closing the second mold the core component produced in the first step is placed into the second mold. The core component fills up most of the cavities within the second mold.

To form the grip component 34 onto the core component 33, the conventional plastic injection mold machine is heated to a grip component processing temperature. The grip component processing temperature is an optimal mold temperature for the specific material selected to form the grip component of the handle 20. A raw grip component material is selected and placed into the hopper of the mold machine. The raw grip component material is fed by gravity into a screw bore.

Preferably, the grip component 34 of the handle 20 is formed from a thermally processed polymeric casting resin. Most preferably, the grip component of the handle is formed from a thermosetting silicone ruber casting resin. Other thermosetting or thermoplastic casting resins can also be employed. The grip component material selected to provide a flexible grip while withstanding the harsh environments encountered in sterilization procedures. The inventor preferred commercially available alternative materials, however blended polymers are also considered.

The second mold is received into the mold machine and heated to the grip component processing temperature. The mold machine closes upon the second mold and again holds it closed at the clamping pressure to prevent the second mold from opening while the raw material is injected into the second mold. Once the second mold is closed, the homogeneously melted grip component material is injected into the second mold under the high pressure. As the grip component material flows into the second mold it fills all voids within the second mold to create the desired grip component shape. The voids in the second mold are actually a cavity between the walls of the second mold and the core component 33 of the handle. This cavity is filled by the softer material of the grip component 34. When the second mold is full, it is held shut for a short time to allow curing of the grip component material onto the core component of the handle 20. The high heat and pressure within the second mold chemically bonds the softer grip material to the core component. At an interface between the core component and the grip component, the core component melts slightly. The grip component at this interface will mix with the melted interface surface of the core component, thereby achieving a strong and moisture tight bond between the core component and the grip component, forming a truly composite handle.

After curing, the second mold is opened and the handle 20 is ejected from the second mold.

The ejected composite handle is checked for defects and prepared for use. Additionally, the handle can also receive identifying names, bar codes and additional colored inserts or colored rings 90, as shown in FIGS. 1 through 6, for personalization, recognition and tracking. Preferably, the colored inserts or colored rings can withstand autoclave and chemclave sterilization.

In compliance with the statutes, the invention has been described in language more or less specific as to structural features and process steps. While this invention is susceptible to embodiment in different forms, the specification illustrates preferred embodiments of the invention with the understanding that the present disclosure is to be considered an exemplification of the principles of the invention, and the disclosure is not intended to limit the invention to the particular embodiments described. Those with ordinary skill in the art will appreciate that other embodiments and variations of the invention are possible which employ the same inventive concepts as described above. Therefore, the invention is not to be limited except by the following claims, as appropriately interpreted in accordance with the doctrine of equivalents.

What is claimed is:

1. A dental curette comprising:
   a dental instrument handle having a first end and a second end,
   the dental instrument handle having a substantially elongate form, and molded from a composite of nonmetallic components; and
   a minimum of a first tip,
   the first tip including a metal dental instrument tool and a non-metal grip component, and
   the first tip received into the first end of said dental instrument handle, and
   said first tip is interchangeably replaceable.

2. The dental instrument of claim 1, further comprising a second tip, the second tip including a metal dental instrument tool and a nonmetalic grip component, and the second tip received into the second end of said dental instrument handle, and
   said second tip is interchangeably replaceable.

3. A dental curette comprising:
   a dental instrument handle which includes a first end and a second end, the dental instrument handle formed from a composite of nonmetallic components; and
   the first tip including a metal dental instrument tool and a nonmetalic grip component removably attached to the first end of said dental instrument handle, the first tip removably attachable from the first end of said dental instrument handle by a disengagable coupling.

4. The dental curette of claim 3, wherein the disengagable coupling is a threaded attachment.

* * * * *